(12) United States Patent
Mohr et al.

(10) Patent No.: US 9,505,676 B2
(45) Date of Patent: Nov. 29, 2016

(54) HYDROCARBON CONVERSION PROCESS

(71) Applicant: ExxonMobil Chemical Patents Inc., Baytown, TX (US)

(72) Inventors: Gary D. Mohr, Houston, TX (US); Jonathan M. McConnachie, Annandale, NJ (US); Paul F. Keusenkothen, Houston, TX (US); Frank Hershkowitz, Basking Ridge, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 847 days.

(21) Appl. No.: 13/858,997

(22) Filed: Apr. 9, 2013

(65) Prior Publication Data

US 2013/0296620 A1 Nov. 7, 2013

Related U.S. Application Data

(60) Provisional application No. 61/642,135, filed on May 3, 2012.

(30) Foreign Application Priority Data

Jun. 29, 2012 (EP) .................................... 12174339

(51) Int. Cl.
| | |
|---|---|
| *C07C 2/86* | (2006.01) |
| *B01J 8/04* | (2006.01) |
| *B01J 19/24* | (2006.01) |
| *C10G 29/22* | (2006.01) |
| *C07C 29/151* | (2006.01) |
| *B01J 8/02* | (2006.01) |

(52) U.S. Cl.
CPC ............. *C07C 2/864* (2013.01); *B01J 8/0292* (2013.01); *B01J 8/0438* (2013.01); *B01J 8/0442* (2013.01); *B01J 8/0492* (2013.01); *B01J 8/0496* (2013.01); *B01J 19/2485* (2013.01); *C07C 29/1518* (2013.01); *C10G 29/22* (2013.01); *B01J 2208/00513* (2013.01); *C10G 2400/30* (2013.01)

(58) Field of Classification Search
CPC ........... C07C 2/864; C07C 1/04; C07C 2/78; B01J 12/00
USPC ............ 585/300 S, 467, 470, 477, 539, 402, 585/500, 943, 314, 300, 330, 310, 639; 208/107, 113, 133, 134
See application file for complete search history.

(56) References Cited

U.S. PATENT DOCUMENTS

| | | |
|---|---|---|
| 4,487,983 A | 12/1984 | Miller et al. |
| 4,585,897 A | 4/1986 | Fields et al. |

(Continued)

FOREIGN PATENT DOCUMENTS

| | | | |
|---|---|---|---|
| GB | 1159035 A | * 7/1969 | ............ B01J 23/72 |

OTHER PUBLICATIONS

Yashima et al., "Alkylation on Synthetic Zeolites", Journal of Catalysis 16, pp. 273-280 (1970).

*Primary Examiner* — Sharon Pregler

(57) ABSTRACT

The invention relates to processes for converting a mixture of hydrocarbon and oxygenate into products containing acetylene and carbon monoxide. The invention also relates to utilizing at least a portion of the acetylene and carbon monoxide for producing xylenes such as p-xylene, utilizing at least a portion of xylenes for producing polymeric fibers, and to equipment useful for these processes.

23 Claims, 4 Drawing Sheets

(56) References Cited

U.S. PATENT DOCUMENTS

| | | | | |
|---|---|---|---|---|
| 5,824,834 A | * | 10/1998 | Bachtler | C01B 3/36 585/537 |
| 6,504,072 B1 | * | 1/2003 | Brown | B01J 29/40 585/464 |
| 7,943,808 B2 | * | 5/2011 | Hershkowitz | B01F 3/02 422/138 |
| 2005/0075524 A1 | | 4/2005 | Feng et al. | |
| 2005/0143613 A1 | | 6/2005 | Dakka et al. | |
| 2007/0144940 A1 | | 6/2007 | Hershkowitz | |
| 2008/0142409 A1 | | 6/2008 | Sankaranarayanan et al. | |
| 2009/0287031 A1 | * | 11/2009 | Mamadov | C07C 2/48 585/403 |
| 2011/0092755 A1 | * | 4/2011 | Lattner | C07C 2/864 585/401 |
| 2011/0201863 A1 | | 8/2011 | Matsushita et al. | |
| 2013/0310601 A1 | | 11/2013 | Mohr et al. | |

\* cited by examiner

HYDROCARBON CONVERSION PROCESS

PRIORITY CLAIM

The present application claims priority to and the benefit of U.S. Ser. No. 61/642,135 filed on May 3, 2012 and EP Application No. 12174339.7 filed Jun. 29, 2012 and entitled, "Hydrocarbon Conversion Process," the disclosure of which is hereby incorporated by reference herein in its entirety.

FIELD OF THE INVENTION

The invention relates to processes for converting a mixture of hydrocarbon and oxygenate into products containing acetylene and carbon monoxide. The invention also relates to utilizing at least a portion of the acetylene and carbon monoxide for producing xylenes such as p-xylene, utilizing at least a portion of xylenes for producing polymeric fibers, and to equipment useful for these processes.

BACKGROUND OF THE INVENTION

Aromatic hydrocarbons, such as benzene, toluene, xylene, etc., are useful as fuels, solvents, and as feeds for various chemical processes. Of the xylenes, para-xylene ("p-xylene") is particularly useful for manufacturing phthalic acids such as terephthalic acid, which is an intermediate in the manufacture of synthetic fibers such as polyester fibers. Xylenes can be produced from naphtha, e.g., by catalytic reforming, with the reformate product containing a mixture of xylene isomers and ethylbenzene. Separating the xylenes from the mixture generally requires stringent separations, e.g., separations utilizing superfractionation and multistage refrigeration steps. Such separations are characterized by complexity, high energy-usage, and high cost. Processes having a relatively large p-xylene yield are desired because they would lessen the need for such stringent separations.

One method for increasing p-xylene yield involves alkylating toluene with methanol over a solid acid catalyst. See, e.g., Yashima et al., in the Journal of Catalysis 16, pp. 273-280 (1970), which discloses selectively producing p-xylene over a temperature in the range of 200° C. to 275° C., with the maximum yield of p-xylene occurring at 225° C.

More recently, U.S. Pat. No. 6,504,072 discloses a method for improving p-xylene yield by alkylating toluene with methanol using a catalyst comprising severely-steamed ZSM-5 and an oxide modifier.

There is a continuing need to provide processes which are highly selective for the production of p-xylene, particularly processes utilizing relatively low-value hydrocarbon feed.

SUMMARY OF THE INVENTION

In an embodiment, the invention relates to a hydrocarbon conversion process, comprising:
(a) providing a first mixture, the first mixture comprising ≥10.0 wt. % hydrocarbon and ≥1.0 wt. % oxygenate, the weight percents being based on the weight of the first mixture;
(b) exposing the first mixture a temperature ≥700° C. in a first region under pyrolysis conditions to produce a second mixture, the second mixture comprising molecular hydrogen, carbon monoxide, and ≥1.0 wt. % of acetylene based on the weight of the second mixture, wherein the second mixture has a molecular hydrogen:carbon monoxide molar ratio ≥2.0 and a carbon monoxide:acetylene molar ratio ≥0.1;
(c) converting at least a portion of the second mixture's acetylene to produce a first intermediate mixture comprising ≥10.0 wt. % aromatic hydrocarbon based on the weight of the intermediate mixture;
(d) reacting at least a portion of the second mixture's carbon monoxide with at least a portion of the second mixture's molecular hydrogen to produce a second intermediate mixture comprising ≥10.0 wt. % alcohol based on the weight of the second intermediate mixture; and
(e) reacting at least a portion of the first intermediate mixture's aromatics with at least a portion of the second intermediate mixture's alcohol to produce a product comprising water and ≥10.0 wt. % p-xylene based on the weight of the product.

DETAILED DESCRIPTION

Figure 1:
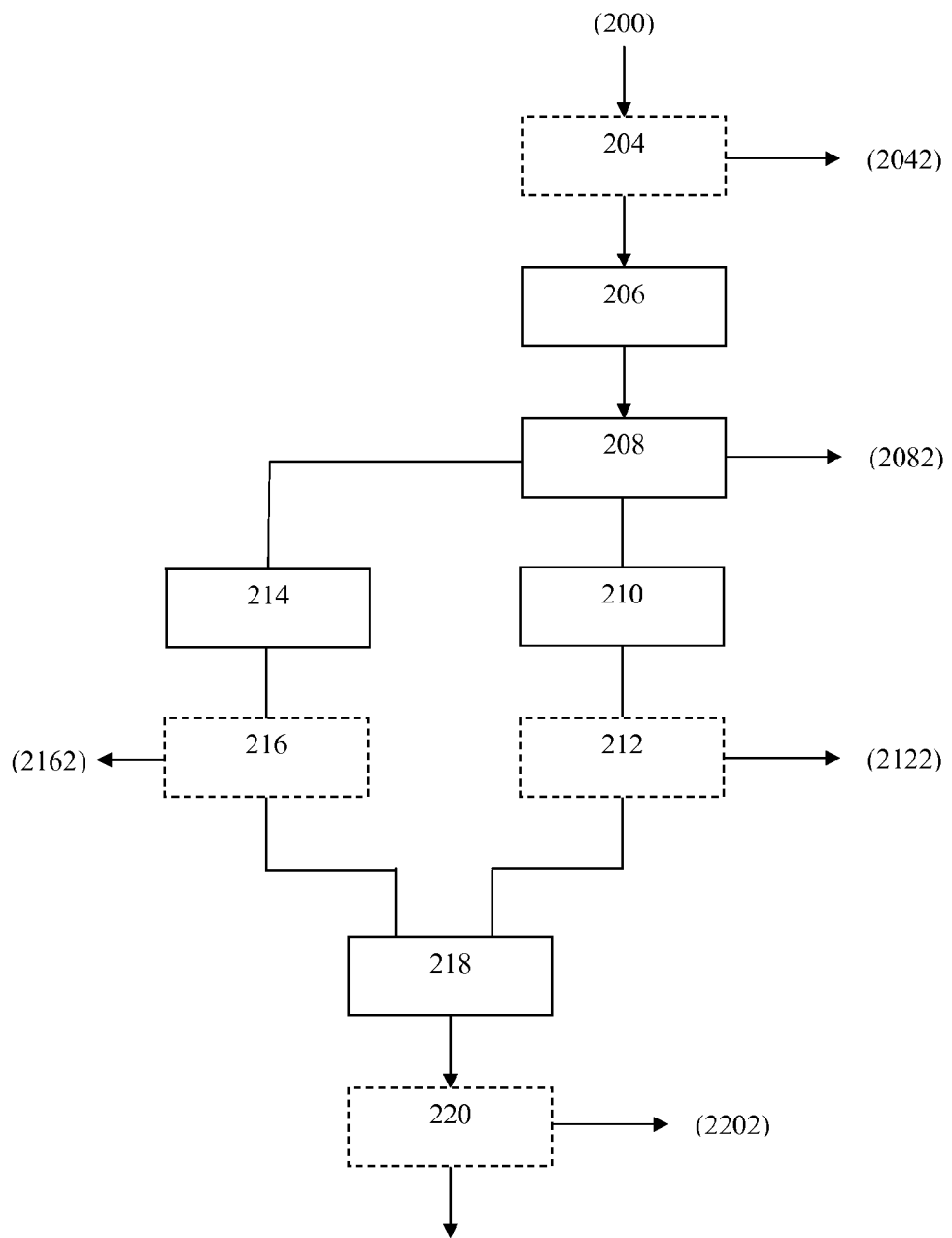
FIG. 1 schematically illustrates embodiments of the invention relating to the conversion of hydrocarbon and oxygenate to a product comprising p-xylene and water. Optional stages are enclosed by dashed lines.

One embodiment of the invention is based on the development of a process for converting a first mixture comprising hydrocarbon and oxygenate to a second mixture comprising acetylene and syngas in relative amounts that are useful for producing aromatics, such as benzene, and alcohol, such as methanol. The process involves exposing the first mixture under pyrolysis conditions to a temperature ≥700° C. (which as used herein means $0.70 \times 10^{3\circ}$ C., i.e., two significant digits), e.g., ≥$1.20 \times 10^{3\circ}$ C. This results in (i) the conversion of a significant amount of the first mixture's hydrocarbon to $C_2$ unsaturates and (ii) the conversion of a significant amount of first mixture's oxygenate to carbon monoxide, with the amount of oxygenate conversion depending on the oxygenate species and the pyrolysis conditions. This aspect of the process is advantageous in that it produces a relatively high yield of two desirable products, acetylene and syngas (the syngas comprising second mixture's carbon monoxide and molecular hydrogen). In an embodiment, at least a portion of the pyrolysis heat utilized in deriving the second mixture from the first mixture is provided by exothermically reacting (e.g., combusting) a fourth mixture which produces a fifth mixture comprising products of the exothermic reaction.

The process further comprises converting at least a portion of the second mixture's acetylene to a first intermediate comprising aromatics such as benzene, reacting at least a portion of the second mixture's carbon monoxide with at least a portion of the second mixture's molecular hydrogen to produce a second intermediate comprising alcohol such as methanol, and then reacting at least a portion of the first intermediate's aromatics with at least a portion of the second intermediate's alcohol to produce a product comprising p-xylene and water. Conventional processes can be utilized for converting the second mixture's acetylene to aromatics and for producing methanol from the second mixture's carbon monoxide and molecular hydrogen. Optionally, at least a portion of the product's water is utilized to produce the first mixture's oxygenate.

Methanol can be produced from the second mixture's carbon monoxide and hydrogen via conventional methods such as those utilizing a catalyst comprising copper, but the invention is not limited thereto. It has been observed that when the first mixture's oxidant comprises carbon dioxide, the second mixture comprises significant amounts of both carbon monoxide and carbon dioxide. This feature can be advantageous since copper-containing methanol synthesis catalysts have appreciable activity for converting the second mixture's carbon dioxide to methanol. In other words, the process provides flexibility for selecting the first mixture's oxygenate components. Conventional acetylene trimerization technology can be utilized for producing aromatics such as benzene from the second mixture's acetylene, but the invention is not limited thereto.

Conventional conversion technology, such as those using one or more zeolite catalysts, can be utilized for converting the first intermediate's benzene and/or toluene to p-xylene, though the invention is not limited to the use of conventional technology for this step. The product's p-xylene can be utilized to produce polymer, e.g., polyethylene terephthalate ("PET"), e.g., by oxidizing (e.g., with air) the product's p-xylene utilizing a solvent such as acetic acid and a catalyst, the catalyst comprising e.g., (i) one or more metals selected from Group VIIb (e.g., Mn) and/or Group VIII (e.g., Co) of the Periodic Table and optionally (ii) at least one promoter selected from Group VIIa (e.g., Br). Conventional processes can be utilized for converting the terephthalic acid to polymer, such as PET, e.g., by processes utilizing (i) an esterification reaction of the terephthalic acid with ethylene glycol or (ii) a transesterification reaction of dimethyl terephthalate and ethylene glycol. Since the second mixture generally contains ethylene, at least a portion of the second mixture's ethylene can be utilized for producing the ethylene glycol, e.g., by oxidizing the ethylene to produce ethylene oxide and then reacting the ethylene oxide with water to produce the ethylene glycol. Polymerizing at least a portion of the second mixture's ethylene, e.g., to produce polyethylene, is also within the scope of the invention. Carbon dioxide byproduct that is produced in some ethylene glycol processes, e.g., those producing an ethylene carbonate intermediate, can be utilized, e.g., for one or more of producing the first mixture; for producing methanol, e.g., the methanol used for making the product's p-xylene; or for recycle to the ethylene glycol process. Water resulting from the reaction of oxygen with the p-xylene to produce the terephthalic acid or from the esterification process can also be utilized in the process, e.g., for one or more of producing the first mixture, for quenching the second mixture, or as a diluent in the conversion of the terephthalic acid to PET.

For the purpose of this description and appended claims, the following terms are defined. The term "hydrocarbon" means molecules (and mixtures thereof) including both carbon atoms and hydrogen atoms, and optionally including other atoms (heteroatoms) such as oxygen, sulfur, and/or nitrogen, wherein the carbon atoms and hydrogen atoms together comprise ≥75.0% of the atoms present in the molecule or mixture of molecules; but excluding molecules comprising ≥10.0 atom % of oxygen atoms. The term "oxygenate" means (i) oxygen atoms and (ii) molecules (and mixtures thereof) which include at least one oxygen atom wherein the oxygen atoms comprise ≥10.0 atom % based on the number of atoms present in the molecule or mixture of molecules, including those molecules which further comprise hydrogen, carbon, sulfur, and nitrogen. The term "molecular hydrogen" means $H_2$.

The term "polymer" means a composition including a plurality of macromolecules, the macromolecules containing recurring units derived from one or more monomers. The macromolecules can have different size, molecular architecture, atomic content, etc. The term "polymer" includes macromolecules such as copolymer, terpolymer, etc. The "Periodic Table of the Elements" means the Periodic Chart of the Elements as tabulated on the inside cover of The Merck Index, 12th Edition, Merck & Co., Inc., 1996.

The terms "pyrolysis" and "pyrolysis chemistry" mean an endothermic reaction conducted at a temperature sufficient for thermally breaking C—C or C—H bonds, optionally aided by a catalyst, e.g., the conversion of hydrocarbons to unsaturates, such as ethylene and acetylene.

The term "reactor" means equipment and combinations thereof for chemical conversion, including reactor combinations and systems such as disclosed in U.S. Patent Application Publication No. 2007/0191664. The term "pyrolysis reactor", as used herein, refers to a reactor, or combination, or system thereof for converting hydrocarbons by at least pyrolysis. The term pyrolysis reactor encompasses, e.g., the combination and system of first and second pyrolysis reactors described in U.S. Patent Application Publication No. 2007/0191664. With respect to pyrolysis reactors, the term "residence time" means the average time duration for non-reacting (non-converting by pyrolysis) molecules (such as He, $N_2$, Ar) having a molecular weight in the range of 4 to 40 to traverse a pyrolysis region of a pyrolysis reactor. The term "pyrolysis stage" means at least one pyrolysis reactor, and optionally including means for conducting one or more feeds thereto and/or one or more products away therefrom. With respect to reactors, the term "region" means a location within a reactor, e.g., a specific volume within a reactor, a specific volume between two reactors and/or the combination of different disjointed volumes in one or more reactors. The term "thermal pyrolysis" means <50.0% of the heat utilized by the pyrolysis is provided by (a) exothermically reacting the pyrolysis feed, e.g., by exothermically reacting an oxidant with hydrocarbon and/or hydrogen of the first mixture and/or (b) contacting the pyrolysis feed with the products of combustion to heat the pyrolysis feed. The term "thermal pyrolysis reactor" means a pyrolysis reactor wherein ≥50.0% of the heat utilized by the pyrolysis is provided by heat transfer from reactor components, e.g., solid surfaces associated with the reactor such as tubulars or bed materials; optionally ≥80.0% or ≥90.0% of the heat utilized by the pyrolysis is provided by such heat transfer.

The term "high-severity" with respect to the pyrolysis of a feed comprising hydrocarbon, e.g., the first mixture, means pyrolysis operating conditions resulting in the conversion to acetylene of ≥10.0 wt. % of the feed's hydrocarbon based on the total weight of the hydrocarbon in the feed. The term "peak pyrolysis gas temperature" means the maximum temperature achieved by the bulk pyrolysis stream gases as they travel through the pyrolysis reactor (e.g., cracking region or radiant region). One skilled in the art will appreciate that temperatures immediately proximate to a solid material may be higher, and may, in some infinitesimal boundary layer, actually approach the solid temperature. However, the pyrolysis temperature referred to herein should be considered a bulk gas temperature, which is a temperature that could be measured by a device (such as a thermocouple) that is not in contact with the solid material.

In an embodiment, a second mixture is derived by pyrolysis of a first mixture, the first mixture being derived from one or more source materials. The term "source materials" means sources comprising hydrocarbon and/or oxygenate. Examples of source materials comprising hydrocarbon include one or more of petroleum-derived streams; syngas (a mixture comprising carbon monoxide and hydrogen), methane; methane-containing streams such as coal bed methane, biogas, associated gas, natural gas, and mixtures or components thereof; synthetic crudes; shale oils; or hydrocarbon streams derived from plant or animal matter. Suitable hydrocarbon source materials include those described in U.S. Pat. Nos. 7,943,808 and 7,544,852, which are incorporated by reference herein in their entirety. Examples of source materials comprising oxygenate include one or more of molecular oxygen, water (e.g., steam), carbon monoxide, carbon dioxide, alcohols (e.g., methanol, ethanol, etc.), acids such as hydrocarbon containing a carboxyl functionality, carbonyls, carbonates, carbamates, carbohydrates, non-volatile oxygenates, etc.

The term "hydrogen content" of a mixture or source material means atomic hydrogen bound to carbon and/or heteroatoms covalently bound thereto and which excludes molecular hydrogen ($H_2$) in the mixture (or source material) expressed as a weight percent based on the weight of the hydrocarbons in the mixture (or source material). Optionally, one or more mixtures and/or source materials comprises non-volatiles. The term "non-volatiles" means molecules and mixtures thereof having a nominal atmospheric boiling point $\geq 570.0°$ C., e.g., refractory oxygenates, refractory hydrocarbons, metals, minerals, etc. American Society of Testing and Materials ("ASTM") methods can be used to determine the nominal atmospheric boiling point (ASTM method 1078) and the amount and properties of such non-volatiles, such as ASTM methods D-6560, D-7061, D-189, D-482, D-524, and D-2415. Non-volatiles that are capable of being combusted are called "combustible non-volatiles". The term non-volatiles encompasses, e.g., coke, ash, soot, resid, metal, mineral, ash-forming asphaltenic, tar, etc., including those formed, e.g., during or after oxidation (e.g., combustion or partial oxidation) and/or pyrolysis, including those which may remain as a residue or deposit in the reaction region. Optionally, one or more mixtures and/or source materials comprises $C_{3+}$. The term "$C_{3+}$" means molecules having at least three carbon atoms, including, e.g., coke and soot, whether those products emerge from the reactor or remain within the pyrolysis reactor.

Representative Embodiments

One embodiment is illustrated schematically in FIG. 1. A source material 200 is conducted to stage 204, the source material comprising hydrocarbon and oxygenate. For example, the source material can comprise (i) $\geq 10.0$ wt. % of methane, e.g., $\geq 25.0$ wt. % methane, such as $\geq 50.0$ wt. % methane and (ii) $\geq 1.0$ wt. % of carbon dioxide, e.g., $\geq 10.0$ wt. % of carbon dioxide, such as $\geq 25.0$ wt. % of carbon dioxide; the weight percents being based on the weight of the source material. Examples of source materials comprising hydrocarbon include one or more of hydrocarbon derived from petroleum; syngas (a mixture comprising carbon monoxide and hydrogen); methane; methane-containing streams, such as coal bed methane, biogas, associated gas, natural gas, and mixtures or components thereof; synthetic crudes; shale oils; or hydrocarbon streams derived from plant or animal matter. Suitable hydrocarbon source materials include those described in U.S. Pat. Nos. 7,943,808 and 7,544,852, which are incorporated by reference herein in their entirety.

The source material can be upgraded in stage 204 to produce the first mixture, e.g., by removing at least a portion of any undesired heteroatom-containing molecules contained in the source material. Such undesired species can be conducted away from stage 204 by conduit 2042. The first mixture, which comprises hydrocarbon and oxygenate, is conducted to stage 206, where the first mixture is exposed to a temperature $\geq 700°$ C. under pyrolysis conditions to produce a second mixture. The second mixture comprises molecular hydrogen, carbon monoxide and $\geq 1.0$ wt. % acetylene based on the weight of the second mixture, wherein (a) the second mixture's carbon monoxide is (i) obtained from the first mixture and/or (ii) derived from the first mixture's oxygenate by the pyrolysis and (b) the second mixture's acetylene is derived from the first mixture's hydrocarbon by the pyrolysis. Heat for the pyrolysis can be obtained from the exothermic reaction of fuel and oxidant components of a fourth mixture, with a fifth mixture comprising products of the endothermic reaction being conducted away.

Although the embodiment of FIG. 1 shows the first mixture being derived from one source material 200, this is not required, and in other embodiments the first mixture is derived from a plurality of source materials, e.g., at least one hydrocarbon source material and at least one oxygenate source material. Optionally, one or more of these source materials is upgraded, e.g., in optional upgrading stages 204a, 204b, etc. (not shown), and with the upgraded effluents being utilized for producing the first mixture.

At least a portion of the second mixture, e.g., a third mixture comprising at least a portion of the second mixture's volatile components, is conducted from stage 206 to stage 208, as shown in FIG. 1. Stage 208 is utilized for separating from the second (or third) mixture at least sixth and seventh mixtures. The sixth mixture comprises at least a portion of the second mixture's acetylene. The seventh mixture comprises (i) at least a portion of the second mixture's carbon monoxide and (ii) at least a portion of the second mixture's molecular hydrogen. Stage 208 can also be utilized for removing from the second mixture (i) one or more of ethylene, non-volatile components such as soot, heteroatom-containing components such as hydrogen sulfide, etc., which are not needed in the downstream steps of the process and/or (ii) excess molecular hydrogen and/or excess carbon monoxide (where "excess" means beyond the amounts of these molecules needed in the downstream steps). These components can be removed before and/or after separation of the sixth and seventh mixtures, and can be conducted away via conduit 2082.

As shown in FIG. 1, the sixth mixture is conducted from stage 208 to stage 214, where at least a portion of the sixth mixture is converted to a first intermediate, the first intermediate comprising aromatics such as benzene obtained by converting at least a portion of the sixth mixture's acetylene. Optional stage 216 can be utilized for removing undesired molecules from the first intermediate, e.g., un-reacted acetylene which can be conducted away via conduit 2162. The seventh mixture is conducted to stage 210, where at least a portion of the seventh mixture is converted to a second intermediate, the second intermediate comprising alcohol, e.g., methanol, obtained by reacting at least a portion of the seventh mixture's molecular hydrogen with at least a portion of the seventh mixture's carbon monoxide. Optional stage 212 can be utilized for removing undesired molecules from the second intermediate, e.g., unreacted carbon monoxide and/or unreacted molecular hydrogen.

At least a portion of the first intermediate and at least a portion of the second intermediate are conducted to stage 218, where at least a portion of the first intermediate's aromatics react with at least a portion of the second intermediate's alcohol to produce a product comprising phthalic acid (such as terephthalic acid) and water, Stage 220 can be utilized for upgrading the product, e.g., by removing from the product a byproduct comprising one or more of water, unreacted aromatics, or unreacted alcohol; the byproduct being conducted away via conduit 2202.

In one embodiment, stage 206 comprises at least one regenerative, reverse-flow thermal pyrolysis reactor system. This reactor system; representative first, and fourth mixtures utilized in such a reactor system; representative second, third, and fifth mixtures produced in such a reactor system; and representative downstream process steps that are compatible with these will now be described in more detail. Although the following embodiments are described in terms of a regenerative, reverse-flow pyrolysis reactor system, the invention is not limited thereto, and this description is not meant to foreclose other embodiments within the broader scope of the invention.

Figure 2:
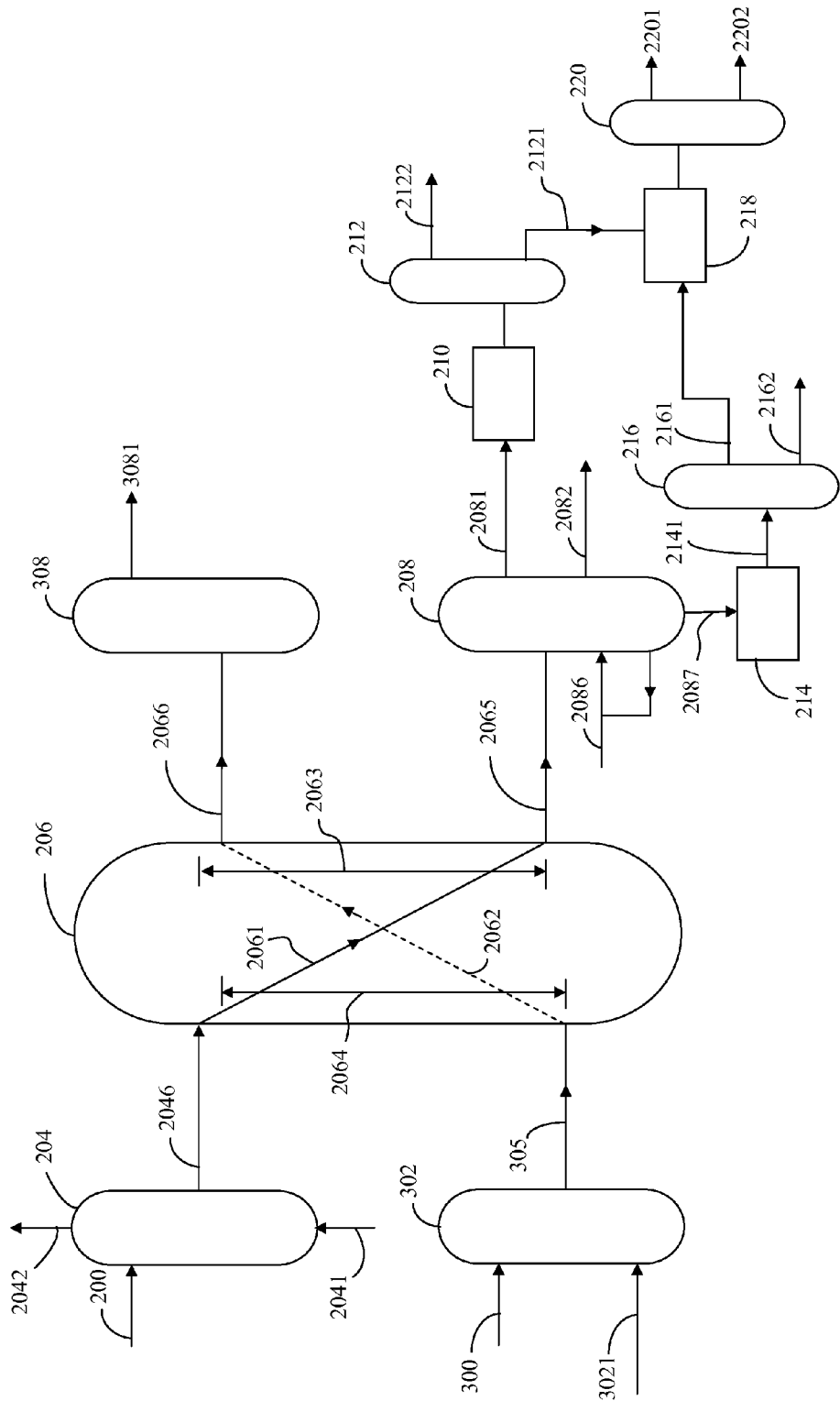
FIG. 2 schematically illustrates an embodiment of the invention utilizing a pyrolysis reactor system.

Representative Embodiment Utilizing a Regenerative, Reverse-Flow Pyrolysis Reactor System An embodiment utilizing a regenerative, reverse-flow thermal pyrolysis reactor system is illustrated schematically in FIG. 2. The first mixture is derived from one or more source materials 200 (e.g., as described above), the source materials optionally being upgraded in optional preparation stage 204. So that the first mixture has the desired composition, preparation stage 204 can be utilized for one or more of (i) separating and conducting away via conduit 2042 one or more of heteroatom-containing molecules such as hydrogen sulfide, hydrocarbon, non-combustible nonvolatiles, oxygenate, molecular hydrogen, or diluent from the source material, (ii) adding via conduit 2041 one or more of hydrocarbon, oxygenate, molecular hydrogen, or diluent to the source material, (iii) thermally upgrading (e.g., coking or visbreaking) the source material, or (iv) catalytically upgrading (e.g., hydroprocessing, such as hydrotreating) the source material, etc. When utilized in connection with one or more of (ii)-(iv), added hydrocarbon, oxygenate, molecular hydrogen, or diluent can be obtained, e.g., from sources external to the process (such as a syngas generation process) or from sources internal to the process when these species are present in excess of that needed for the downstream steps. For example, light saturated hydrocarbon, such as methane; diluent; excess molecular hydrogen; and/or excess oxygenate (e.g., excess carbon monoxide) can be obtained from the water byproduct, the second intermediate, or from one or more of the second, third, fifth, or seventh mixtures.

Optionally, the amount of one or more of molecular hydrogen, light saturated hydrocarbon, oxygenate, or diluent in the first mixture can be increased by conducting one or more of these to stage 204 from one of the following sources:

(i) Molecular hydrogen can be obtained (a) from the process via conduits 2082 and/or 2122 or (b) from an external source, e.g., an optional synthesis gas generation process;
(ii) Hydrocarbon (e.g., light saturated hydrocarbon) can be obtained from the process, e.g., via conduit 2082;
(iii) Oxygenate can be obtained, e.g., (a) from the fifth mixture, (b) from conduit 2082, (c) from steam, e.g., steam generated in a process cooler, and/or (d) from a source external to the process, such as a syngas generation process; and (iv) Diluent can be obtained via conduit 2082 when stage 208 is utilized for separating diluent from the second mixture.

Preparation stage 204 is optional. In other words, the first mixture can comprise (or consist essentially of, or even consist of) hydrocarbon and oxygenate obtained directly from source material(s) 200, such as natural gas and air, optionally with no intervening process steps.

First Mixture

The first mixture can comprise (i) ≥10.0 wt. % hydrocarbon and (ii) ≥10.0 wt. % oxygenate, and optionally further comprises (iii) molecular hydrogen and (iv) diluent, the weight percents being based on the weight of the first mixture. For example, the first mixture can comprise (i) ≥25.0 wt. % of hydrocarbon, e.g., ≥50.0 wt. % of hydrocarbon and (ii) ≥5.0 wt. % of oxygenate, e.g., ≥10.0 wt. % of oxygenate, such as ≥25.0 wt. % of oxygenate. The type of hydrocarbon is not critical; e.g., the hydrocarbon can even comprise hydrocarbon non-volatiles, including those that are not in the gas phase at the temperature, pressure, and composition conditions subsisting at the inlet to the pyrolysis reactor.

In an embodiment, the hydrocarbon and oxygenate of the first mixture are derived from one or more source materials, as defined in the preceding section. For example, in one embodiment the first and second source materials are conducted separately to a pyrolysis reactor, wherein (i) the first source material comprises hydrocarbon and (ii) the second source material comprises oxygenate, with the first and second source materials being combined to produce the first mixture proximate to (e.g., within) the pyrolysis reactor. Optionally, the hydrocarbon source material has a hydrogen content in the range of 6.0 wt. % to 25.0 wt. %, 8.0 wt. % to 20.0 wt. % (e.g., not natural gas), or 20.0 wt. % to 25.0 wt. % (e.g., natural gas). In a particular embodiment, the hydrocarbon of the first mixture is derived from natural gas (e.g., a methane-containing gas of synthetic and/or geological origin). The first mixture can comprise, e.g., upgraded natural gas (such as natural gas that has been sweetened and/or dehydrated). Besides methane, natural gas commonly includes other hydrocarbons (such as ethane and other alkanes), generally in amounts greater than or equal to the amount of methane in the natural gas on a weight basis. Optionally, the natural gas further comprises oxygenate (e.g., water, $CO_2$, etc.) and/or diluent (e.g., hydrogen sulfide, nitrogen, etc.), which can be used as a source of at least a portion of the oxygenate (in the case of water and/or $CO_2$) and/or diluent (in the case of nitrogen) in the first mixture. One feature of the invention is that a natural gas containing a significant amount of $CO_2$, e.g., ≥20.0 mole % $CO_2$ per mole of the natural gas, can be converted into technologically important products such as terephthalic acid and polymer. Optionally, the oxygenate of the first mixture is derived from the same source material as the hydrocarbon (e.g., both the hydrocarbon and oxygenate are derived from natural gas). Alternatively, the oxygenate is derived from at least a second source material, e.g., one comprising one or more of oxygen ($O_2$), water (e.g., steam), carbon monoxide, carbon dioxide, acid (e.g., organic acids such as hydrocarbon containing a carboxyl functionality), carbonyls, carbonates, carbamates, carbohydrates, non-volatile oxygenates, etc.

When the first mixture's oxygenate comprises ≥90.0 wt. % carbon monoxide based on the weight of the first mixture's oxygenate, the first mixture (i) has a ratio of oxygen atoms to carbon atoms ("O:C") ≥0.1, e.g., in the range of 0.1 to 2.0, such as in the range of 0.1 to 0.5, and (ii) comprises 10.0 wt. % to 95.0 wt. % hydrocarbon, e.g., 15.0 wt. % to 85.0 wt. %; 5.0 wt. % to 60.0 wt. % oxygenate, e.g., 10.0 wt. % to 60.0 wt. %; and 0.0 wt. % to 30.0 wt. % molecular hydrogen, e.g., 5.0 wt. % to 25.0 wt. %, the weight percents being based on the weight of the first mixture. The O:C atomic ratio is defined as the ratio of oxygen atoms (as the total number of oxygen atoms in the first mixture) to carbon atoms (as all carbon atoms in the first mixture that are not bound to oxygen atoms, e.g., as can be determined by Nuclear Magnetic Resonance Spectroscopy). For example, the denominator of this ratio can be equal to the number of carbon atoms bound to the first mixture's hydrocarbon. When an oxygenate other than carbon monoxide is utilized, the amount of oxygenate (as defined by the O:C ratio) is equal to (a) the amount of oxygenate that would have been used if the oxygenate were carbon monoxide divided by (b) the Effectiveness Factor corresponding to the oxygenate that is actually used. For example, the first mixture O:C ratio is set equal to (a) divided by (b), where (a) is the O:C ratio that would have been used if the oxygenate were carbon monoxide and (b) is the Effectiveness Factor corresponding to the oxygenate that is actually used. The Effectiveness Factor can be readily determined by one skilled in the art of pyrolysis as the fraction of the first mixture oxygenate oxygen atoms that emerge from pyrolysis as carbon monoxide molecules in the second mixture. The Effectiveness Factors for selected oxygenates is set out in the following table, those Effectiveness Factors being based on exposing a feed comprising methane, molecular hydrogen, and oxygenate, e.g., the first mixture, under a wide range of conditions effective to result in a 50 to 70% conversion of the methane, including peak pyrolysis temperatures ranging from 1400° C. to 1800° C., pressures from 1.3 to 2.0 bar (absolute), and residence times from about 1 to 50 millisecond. It has been found that the Effectiveness Factor, except for that of molecular oxygen, is approximately constant over this broad range, as long as conditions are effective to result in about 50 to 70% hydrocarbon conversion. While not wishing to be bound by any theory or model, it is believed that the variation observed in the Effectiveness Factor of molecular oxygen as a function of pyrolysis conditions results at least in part from the reaction of the molecular oxygen with the first mixture's hydrocarbon, which leads to changes in pyrolysis heat balance. When the oxygenate is a mixture of two or more oxygenates, the mixture's Effectiveness Factor is approximately equal to the linear combination of the individual oxygenate's Effectiveness Factors. For example, when the oxygenate is a mixture of X mole % of carbon monoxide, Y mole % of water, and Z mole % of carbon dioxide, the mixture's Effectiveness Factor $=X \cdot 1.0 + Y \cdot 0.05 + Z \cdot 0.45$. In an embodiment, the Effectiveness Factor is ≥0.10, e.g., ≥0.2, such as ≥0.4. In an embodiment, the oxygenate is one or more of water, molecular oxygen, carbon dioxide, or carbon monoxide. In an embodiment, the oxygenate is one or more of (i) a lower-cost oxygenate, such as air or water, or (ii) oxygenate such as carbon dioxide, that is naturally present in the hydrocarbon source material.

TABLE

| Oxygenate | Effectiveness Factor |
|---|---|
| Carbon Monoxide | 1.0 |
| Water | 0.05 |
| Molecular Oxygen ($O_2$) | 0.15 |
| Carbon Dioxide | 0.45 |
| Methanol | 0.95 |
| Ethanol | 0.65 |

The amount of oxygenate in the first mixture can be selected based on (i) the types and relative amounts of oxygenate(s) subjected to the pyrolysis, (ii) the amount of acetylene in the second mixture that will be utilized to produce the desired p-xylene precursors for use in stage 218, (iii) the amount of carbon monoxide (and/or carbon dioxide) of the second mixture that will be utilized for producing methanol, and (iv) the amount of methanol utilized for converting the p-xylene precursors (principally benzene and/or toluene) to p-xylene. Optionally, the amount of oxygenate in the second mixture is selected to produce within approximately $^{+/-}25.0\%$, e.g., $^{+/-}10.0\%$, of the stoichiometric amount of carbon monoxide and/or carbon dioxide necessary for producing an amount of methanol that is within approximately $^{+/-}25.0\%$, e.g., $^{+/-}10.0\%$, of the amount needed to stoichiometrically convert the p-xylene precursors of stage 218 (generally benzene and/or toluene) to xylene.

When the first mixture comprises molecular hydrogen, the first mixture optionally has a molecular hydrogen to carbon (as all carbon atoms in the first mixture that are not bound to oxygen atoms, e.g., as can be determined by Nuclear Magnetic Resonance Spectroscopy) molar ratio in the range of from 0.0 to 5.0, e.g., 0.1 to 4.0, such as 1.0 to 3.0 or 1.0 to 2.0. Optionally, the first mixture has a hydrogen (all hydrogen atoms in the first mixture regardless of atomic or molecular form) to carbon (all carbon atoms in the first mixture regardless of atomic or molecular form) atomic ratio in the range of from 1.0 to 15.0, e.g., in the range of from 3.0 to 8.0.

Optionally, the first mixture further comprises diluent, e.g., ≥1.0 wt. % of diluent based on the weight of the first mixture. Suitable diluents (which can be a diluent mixture) include one or more of nitrogen ($N_2$), hydrogen sulfide, $C_{4+}$ mercaptans, amines, mixtures of amines, non-hydrocarbon non-volatiles (whether combustible or not) including refractory inorganics such as refractory oxygenates, inert gas (including inert gas mixtures), etc. In an embodiment, the first mixture comprises ≤10.0 wt. % diluent.

In an embodiment, the first mixture comprises a total amount of non-combustible non-volatiles (e.g., ash, ASTM D-189), from all sources, ≤2.0 parts per million weight (ppmw) based on the weight of the first mixture, e.g., ≤1.0 ppmw. Optionally, the first mixture comprises a total amount of combustible non-volatiles (e.g., tar, asphaltenes, ASTM D-6560) in the first mixture, from all sources, ≤5 wt. % based on the weight of the hydrocarbon in the first mixture, e.g., ≤1.0 wt. %, such as ≤100.0 ppmw or ≤10.0 ppmw, provided the presence of the combustible non-volatiles does not result in ≥2.0 ppmw (e.g., ≥1.0 ppmw) based on the weight of the second mixture.

In an embodiment, at least 15.0 wt. % of the molecular hydrogen in the first mixture (based on the total weight of molecular hydrogen in the first mixture) is molecular hydrogen derived from the second mixture or one or more products thereof. In another embodiment, the first mixture comprises ≥50.0 ppmw sulfur based on the weight of the first mixture.

One suitable process for deriving the second mixture from the first mixture will now be described in more detail. In this embodiment, the second mixture is derived from the first mixture by exposing the first mixture to pyrolysis conditions in a regenerative, reverse-flow pyrolysis reactor. The invention is not limited to this embodiment, and this description should not be construed as foreclosing other embodiments for deriving the second mixture, such as those utilizing other pyrolysis or partial oxidation reactors.

Regenerative, Reverse-Flow Thermal Pyrolysis System

Figure 3:
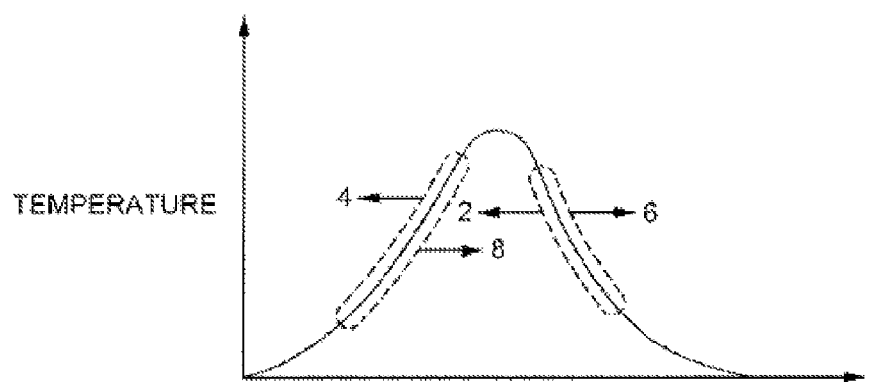
FIG. 3 schematically illustrates an embodiment of the invention utilizing a regenerative, reverse-flow pyrolysis reactor system.
Figure 3:
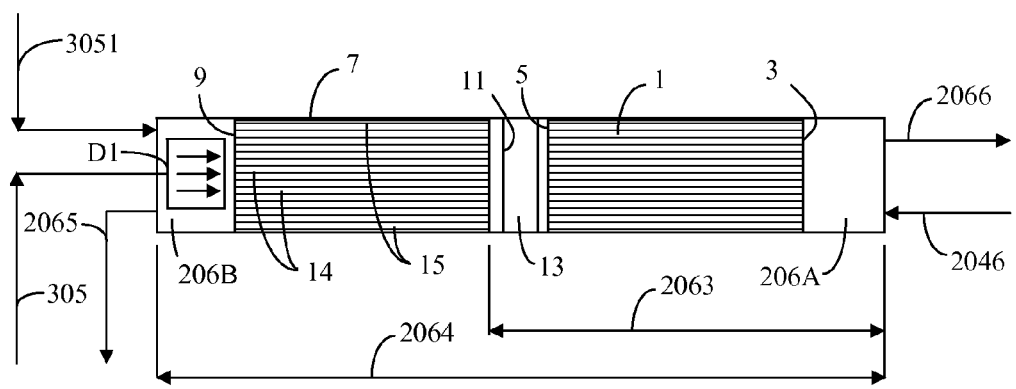

In an embodiment, the second mixture is derived from the first mixture in a reverse-flow, regenerative bed reactor system. Such reactor systems can be used for operating (e.g., continuously or semi-continuously) a two-step asymmetric cycle reaction, e.g., a cycle comprising an oxidation (regeneration) step and a pyrolysis (reforming) step. Suitable reactor systems include, those described in U.S. Patent Application Publication No. 2007/0191664, U.S. Pat. Nos. 7,491,250 and 7,943,808; U.S. Patent Application Ser. No. 61/349,464; and U.S. Patent Application Publication Nos. 2007/0144940 and 2008/0142409, all of which are incorporated by reference herein in their entirety. An example of a representative reverse-flow, regenerative bed reactor system is depicted in FIG. 3. The reactor comprises three zones, a first ("recuperator") zone 7, a mixing-distributing zone 13, and a second ("reaction") zone 1. Zones 1 and 7 each comprise at least one regenerative bed, where the term "regenerative bed" means a reactor bed comprising material that is effective in storing and transferring heat. In an embodiment, the regenerative beds comprise bedding or packing material such as glass or ceramic beads or spheres, metal beads or spheres, ceramic (including, e.g., alumina, silica, yttria, zirconia, etc., and mixtures thereof) or metal honeycomb materials, ceramic tubes, extruded monoliths, catalysts, etc. The first and second reactor beds can be of the same shape and size, but this is not required. Zone 13 generally comprises at least one mixer-distributor for combining fuel and oxidant during regeneration of the regenerative, reverse-flow reactor system.

In an embodiment, at least one of the first or second reactor beds comprises a honeycomb monolith. Although honeycombs can have a circular cross section, this is not required, and the term is not limited to any particular monolithic structure, shape, or topology. In embodiments where a honeycomb monolith is used, the honeycomb monolith is believed to enable low pressure loss transference while providing contact time and heat transfer.

The reactor system is heated for the pyrolysis step, with at least a portion of the heat utilized by the endothermic pyrolysis step being provided by the oxidation step. The heating can occur in exothermic reaction region 2063, which can be located, e.g., between a first point proximate to the downstream end 11 of first reactor 7 and a second point proximate to the downstream end 3 of second reactor 1; "downstream" in this case being with respect to the average flow of fuel and oxidant.

A first reactant, comprising, e.g., fuel, and a second reactant, comprising, e.g., an oxidant such as air, are generally conducted to a location proximate to mixing zone 13. The first and second reactants are distributed and mixed as they traverse zone 13, and the combined reactants together with any oxidation products are then conducted away from zone 13 via passages in second reactor 1.

The oxidation step results in a high temperature zone in the reactor system's temperature profile, at least a portion of the high temperature zone being located in region 2063. The temperature profile is illustrated schematically as a Gaussian-like shape in FIG. 3.

The oxidation step thus includes the following features: (i) heating of zone 13 and the second reactor 1 by transferring at least a portion of the heat of combustion to the reactor system downstream of the end 11 of the first reactor 7 and (ii) by transferring at least a portion of the sensible heat recovered by the first and second reactants in an upstream region of the first reactor (upstream with respect to the flow of the first and second reactants) toward one or more of the downstream region of the first reactor, region 13, or the second reactor in order to thermally regenerate the reactor system. Accordingly, at least a segment of each of the right-hand and left-hand edges of the temperature profile translate downstream from their starting locations at the beginning of the oxidation step, as shown in FIG. 3 by arrows 6 and 8. After the reactor system is heated, the flow-direction of gasses traversing the reactor system is reversed for the pyrolysis step. The oxidation step and pyrolysis step will now be described in more detail.

The Pyrolysis Step

At the start of the pyrolysis step, reaction zone 1 is at an elevated temperature, and the recuperator zone 7 is at a lower temperature than the reaction zone 1. The first mixture (the reactant feed, e.g., a pyrolysis feed) is introduced via a conduit 2046, into a first end 3 of the reaction zone 1.

In the embodiment of FIG. 3, the pyrolysis region 2064 can be located, e.g., between a first point proximate to the upstream end 3 of the second reactor 1 and a second point proximate to the downstream end 9 of first reactor 7, "upstream" and "downstream" being with respect to the average flow of the first mixture. It should be appreciated that the invention can be practiced without precisely defining (a) the boundaries of regions 2063 and 2064. Although region 2063 (the exothermic reaction region) is at least partially coextensive with pyrolysis region 2064, the upstream end of region 2063 ("upstream" with respect to the average flow of the fourth mixture) is generally proximate to the location where sufficient fuel and oxidant combine to produce an exothermic reaction. The downstream (with respect to the average flow of the first mixture) end of region 2063 is generally proximate to the downstream end of second reactor 1 as shown in FIG. 3, though this is not required, and in at least one embodiment the downstream end of region 2063 is located further downstream, e.g., in conduit 2066. In at least one of the embodiments represented by FIG. 3, the upstream end of pyrolysis region 2064 is proximate to the upstream end 3 of the second reactor 1. The downstream end of pyrolysis region 2064 can be, e.g., proximate to the downstream end 9 of the first reactor 7. Optionally, a major amount (e.g., >50%) of the heat abstracted from the reactor system during the pyrolysis occurs in the portion of region 2064 that is coextensive with region 2063.

The pyrolysis can be conducted, e.g., under high-severity pyrolysis conditions. The term "high-severity" with respect to the pyrolysis of a feed comprising hydrocarbon, e.g., the first mixture, means pyrolysis operating conditions resulting in the conversion to acetylene of $\geq 10.0$ wt. % of the feed's hydrocarbon based on the total weight of hydrocarbon in the feed. The pyrolysis can be conducted under thermal pyrolysis conditions, e.g., high-severity thermal pyrolysis conditions.

In an embodiment, the first mixture is conducted to the pyrolysis stage 206 wherein it is exposed to a temperature $\geq 1.20 \times 10^{3\circ}$ C. under thermal pyrolysis conditions, e.g., high-severity, thermal pyrolysis conditions, to convert at least a portion of the first mixture to the second mixture. Under these conditions, $\geq 50.0$ mole %, e.g., $\geq 60.0$ mole %, such as $\geq 70.0$ mole % of the first mixture's hydrocarbon is converted by the pyrolysis, per mole of the first mixture's hydrocarbon. At least a portion of the second mixture, e.g., a vapor-phase portion which comprises acetylene, ethylene, molecular hydrogen, carbon monoxide, and saturated hydrocarbon, is conducted away from the reactor system, e.g., to an optional upgrading stage. A portion of the second mixture, e.g., a non-volatile portion (such as coke and/or soot) can remain in the stage 206, e.g., as a deposit.

In an embodiment, the pyrolysis is conducted under high-severity thermal pyrolysis conditions, e.g., by exposing the first mixture to temperature in the range of about $1.40 \times 10^{3\circ}$ C. to about $2.30 \times 10^{3\circ}$ C., e.g., in the range of about $1.45 \times 10^{3\circ}$ C. to about $1.80 \times 10^{3\circ}$ C. at a residence time ≤about 0.3 seconds, e.g., ≤0.05 seconds. Optionally, the residence time is ≤0.05 seconds, such as ≤0.02 seconds. Optionally, ≥25.0 wt. % (such as of the ≥50.0 wt. % or ≥75.0 wt. %) of the first mixture achieves a peak pyrolysis gas temperature ≥$1.40 \times 10^{3\circ}$ C., e.g., in the range of about $1.50 \times 10^{3\circ}$ C. to about $1.675 \times 10^{3\circ}$ C., based on the weight of the first mixture.

In an embodiment, the pyrolysis is conducted for a time duration ($t_1$) sufficient for exposing ≥50.0 wt. %, e.g., ≥75.0 wt. %, such as ≥90.0 wt. % of the first mixture (based on the weight of the first mixture) to pyrolysis conditions for a residence time ≤about 0.3 seconds, e.g., ≤0.05 seconds. In an embodiment, $t_1$ is ≤10.0 seconds, e.g., ≤5.0 seconds, such as ≤1.0 seconds. Optionally, $t_1$ is in the range of $1.0 \times 10^{-3}$ seconds to 10.0 seconds.

In an embodiment, the pyrolysis step includes one or more of the following conditions: the first mixture achieves a peak pyrolysis gas temperature ≥$1.40 \times 10^{3\circ}$ C., e.g., in the range of $1.45 \times 10^{3\circ}$ C. to $2.20 \times 10^{3\circ}$ C., such as, $1.50 \times 10^{3\circ}$ C. to $1.90 \times 10^{3\circ}$ C., or $1.60 \times 10^{3\circ}$ C. to $1.70 \times 10^{3\circ}$ C.; a total pressure ≥1.0 bar (absolute), e.g., in the range of 1.0 bar to about 15 bar, such as in the range of 2.0 bar to 10.0 bar; a residence time (during high severity conditions) ≤0.1 seconds, e.g., ≤$5.0 \times 10^{-2}$ seconds, such as ≤$5.0 \times 10^{-3}$ seconds and/or a $t_1$ in the range of $1.0 \times 10^{-3}$ seconds to 10.0 seconds.

Continuing with reference to FIG. 3, the first mixture abstracts heat from the reactor system, resulting in the derivation of the second mixture from the first by pyrolysis. As this step proceeds, a shift in the temperature profile occurs, e.g., a shift in at least a segment of the right-hand edge of the temperature profile (the segment being schematically encompassed by a dashed boundary for the purpose of illustration), the direction of the shift being indicated by arrow 2. The amount of this shift can be influenced by, e.g., the heat transfer properties of the reactor system. At least a portion of the second mixture, e.g., the portion in the vapor phase, is conducted from the downstream end 5 of the second reactor 1 to the upstream end 11 of the first reactor 7, and is conducted away from the first reactor via conduit 2065 proximate to the downstream end 9, as shown. At the start of pyrolysis, the first reactor 7 has a temperature less than that of the second reactor 1. As the second mixture traverses the first reactor 7, the second mixture is quenched (e.g., cooled) to a temperature approaching that of the downstream end 9 of the first reactor. As the second mixture is quenched in the first reactor 7, at least a segment of the left-hand edge of the temperature profile moves toward the downstream end 9 of the first reactor 7 as indicated by arrow 4, the segment being schematically encompassed by a dashed boundary for the purpose of illustration. In at least one of the embodiments represented by FIG. 3, the upstream end of pyrolysis region 2064 is proximate to the upstream end 3 of the second reactor 1. The downstream end of pyrolysis region 2064 is proximate to the downstream end 9 of the first reactor 7. Since the quenching heats the first reactor 7, the oxidation step optionally includes cooling the first reactor, e.g., to shift at least a segment of the left-hand edge of the temperature profile away from end 9 of the first reactor 7, as illustrated schematically by arrow 8 in FIG. 3.

The second and third mixtures produced by pyrolysing the specified first mixture under the specified pyrolysis conditions will now be described in more detail.

The Second and Third Mixtures

When the specified first mixture is pyrolysed under the specified pyrolysis conditions, the second mixture comprises molecular hydrogen, carbon monoxide, and ≥1.0 wt. % of acetylene based on the weight of the second mixture, the second mixture having a CO:acetylene molar ratio in the range of 0.10 to 2.0. Optionally, the second mixture has one or more of the following additional properties: an acetylene: ethylene molar ratio ≥0.5, such as in the range of about 0.5 to about 20.0, e.g., about 1.20 to about 10.0, or about 2.0 to about 10.0; a molecular hydrogen:acetylene molar ratio ≥0.1, or ≥0.75, or ≥3.0, e.g., in the range of 3.0 to 20.0; a water content ≤50.0 wt. % based on the weight of the second mixture, e.g., 25.0 wt. %, such as ≤10.0 wt. %; or a carbon dioxide:$C_2$ unsaturates molar ratio ≤1.0, e.g., ≤0.30. Optionally, the second mixture comprises ≥1.0 wt. %, methane e.g., 2.0 wt. % to 50.0 wt. %; ≥1.0 wt. % carbon monoxide, e.g., 2.0 wt. % to 50.0 wt. %, such as 5.0 wt. % to 35.0 wt. %; ≥1.0 wt. % molecular hydrogen, e.g., 2.0 wt. % to 50.0 wt. %; ≥2.0 wt. % acetylene, e.g., 2.0 wt. % to 40.0 wt. %; ≥1.0 wt. % ethylene, e.g., 2.0 wt. % to 70.0 wt. %, such as 2.0 wt. % to 20.0 wt. %; and ≥1.0 wt. % $C_{3+}$, e.g., 2.0 wt. % to 50.0 wt. %, the weight percents being based on the weight of the second mixture.

In an embodiment, at least a portion of the second mixture's non-volatiles remain in stage 206, e.g., as coke or soot. A third mixture comprising at least a portion of the second mixture that is in the vapor phase at the downstream end of stage 206 is conducted to stage 208 as shown in FIG. 1 and FIG. 2. Optionally, the third mixture has substantially the same composition as the second mixture, except the third mixture has a non-volatile content that is ≤0.9 times the non-volatile content of the second mixture on a weight basis, e.g., ≤0.5 times, such as ≤0.1 times.

Optionally, the third mixture is substantially free of $C_{3+}$, e.g., $C_{3+}$ hydrocarbon. For example, the third mixture can comprise $C_{3+}$ hydrocarbon in an amount ≤1.0 wt. %, e.g., ≤0.01 wt. % based on the weight of the third mixture.

Optionally, the mole percents of carbon monoxide, molecular hydrogen, and acetylene in the third mixture are in the following ranges: carbon monoxide in the range of from about 1.0 mole % to 50.0 mole %, such as from about 1.0 mole % to 35 mole %; molecular hydrogen in the range of from about 1.0 mole % to 98.0 mole %, e.g., about 2.0 mole % to about 95.0 mole %, such as about 10.0 mole % to 80.0 mole %; and acetylene in the range of from about 0.1 mole % to 35.0 mole %, such as from about 1.0 mole % to 35.0 mole %, the mole percents being based on the number of moles of carbon monoxide, molecular hydrogen, and acetylene per mole of the third mixture.

In an embodiment, the third mixture has an amount of carbon monoxide and molecular hydrogen with respect to the amount of acetylene that is substantially a stoichiometric amount for converting ≥90.0 wt. % of the third mixture's acetylene (e.g., ≥95.0 wt. %, such as ≥99.0 wt. %) to phthalic acid, such as terephthalic acid, based on the weight of the third mixture. In this regard, a substantially stoichiometric conversion of these species means that per mole of the third mixture (i) the number of moles of carbon monoxide is equal to 0.67 (within +/−10%) times the number of moles of acetylene and (ii) the number of moles of molecular hydrogen is equal to 1.33 (within +/−10%) times the number of moles of acetylene. Optionally, the third mixture comprises 0.0 wt. % to 50.0 wt. % acetylene (such as 0.1 wt. % to 10.0 wt. %), 0.0 wt. % to 50.0 wt. % ethylene, 1.0 wt. % to 60.0 wt. % carbon monoxide, and 0.1 wt. % to 30.0 wt. % molecular hydrogen, with the amount of molecular hydrogen being in the range from 0.2 to 20.0 times the stoichiometric amount for converting the carbon monoxide to methanol.

Producing the second mixture from the first mixture by pyrolysis is an endothermic reaction, which withdraws heat from the pyrolysis reactor system. When the reactor system is cycled continuously or semi-continuously, at least a portion of the heat utilized by the pyrolysis steps is replaced by heat produced during the intervening oxidation steps, with one cycle of the reactor system comprising an oxidation step and a pyrolysis step. The oxidation (regeneration) step will now be described in more detail with reference to FIGS. 2, 3, and 4.

The Oxidation Step

Regeneration entails transferring heat from (i) the mixing-distributing zone 13 and optionally (ii) from recuperator zone 7 to the reaction zone 1, to thermally regenerate the reactor system for a pyrolysis step. A fourth mixture, (the regeneration gas, e.g., the combustion gas) is produced proximate to zone 13 by mixing and distributing the first and second reactants, e.g., fuel and oxidant. The first reactant (comprising fuel) is conducted to recuperator zone 7 via conduit 305. The second reactant (comprising oxidant) is conducted to recuperator zone 7 via conduit 3051. Optionally, first distribution means (D1) can be utilized for conducting the first reactant into fuel passages 14 and/or second distributor means (e.g., plenum 206B) can be utilized for conducting the second reactant into oxidant passages 15, the fuel passages and oxidant passages being located within recuperator zone 7. Since the fuel and oxidant passages are substantially independent flow paths (e.g., there is little or no fluid communication one with the other) mixing of the first and second reactants generally does not occur until zone 13, where the first and second reactants combine to produce the fourth mixture. A fifth mixture, derived from at least in part from the oxidation of at least a portion of the fourth mixture's fuel component, is conducted away from the reactor system via plenum 206A and conduit 2066.

The first and second reactants exit recuperator zone 7, and combine in zone 13 to produce the fourth mixture. By keeping these reactants substantially separated upstream of zone 13, upstream with respect to the average flow of the first and second reactants, the heat (i) conveyed from the recuperator zone toward the regenerator zone and (ii) released during the exothermic reaction is directed towards regions of the reactor system that are beneficial for the pyrolysis. The term "substantially separated", means that ≤50.0 wt. %, e.g., ≤25.0 wt. %, of the first reactant's fuel component is consumed by reaction with the second reactant's oxidant component upstream of zone 13, based on the weight of the first reactant's fuel component conveyed to distributor (D1). In this manner, the majority of the heat release from the reaction of the fourth mixture's fuel and oxidant components will not take place until the gases have exited from the recuperator zone 7 into mixing-distributing zone 13. Optionally, passages 14 and 15 of recuperator zone 7 are oriented substantially parallel to the direction of the average flow of fuel and oxidant. Such passages are provided, for example, by regenerative beds comprised of extruded honeycomb monoliths, packing, stacked layers of corrugated materials, etc. When the recuperator zone 7 includes a packed bed or foam monolith materials (not shown), these bed materials should be configured to keep the first and second reactants substantially separated. Radial dispersion and the amount of first-reactant-second reactant mixing can be measured and/or calculated as described in U.S. Pat. No. 7,815,873.

Figure 4:
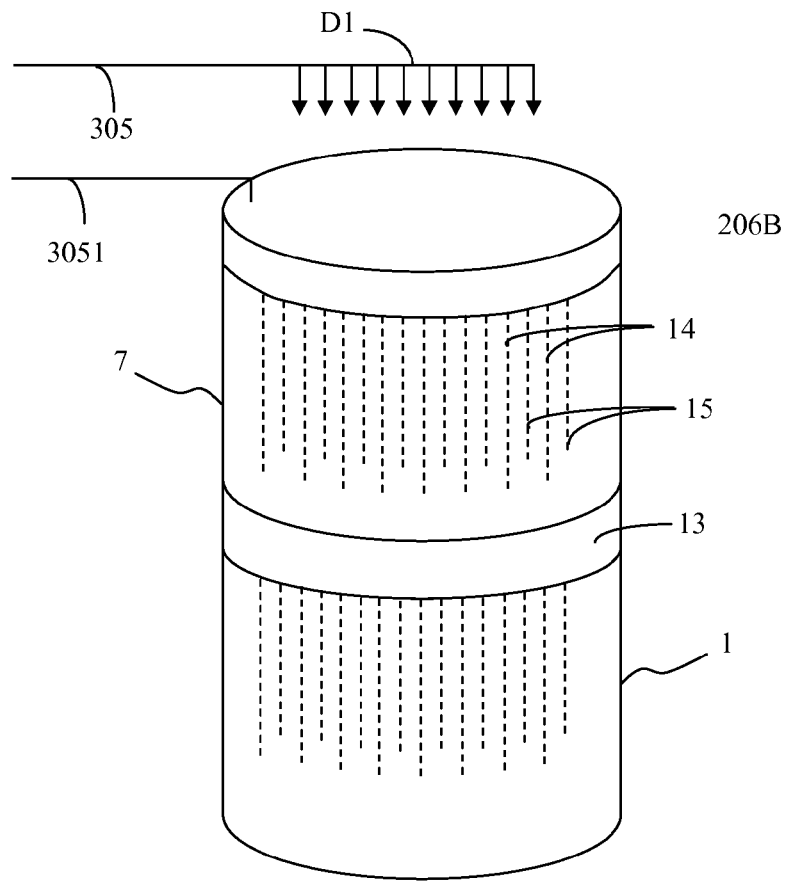
FIGS. 4 and 4a illustrate one embodiment of a regenerative, reverse-flow pyrolysis reactor system.
Figure 4A:
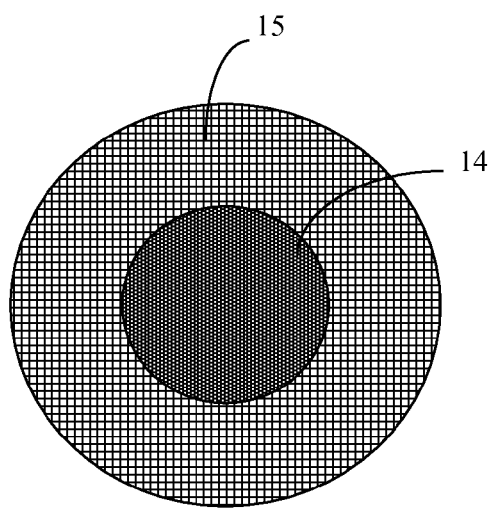

FIGS. 3 and 4 schematically show a flow distributor D1 for directing fuel into passages 14. Distributor D1 has a plurality of apertures (shown as small arrows in FIGS. 3 and 4) aligned with passages 14. Plenum 206B provides for the flow of oxidant into passages 15. The apertures of D1 can be aligned with, but are not sealed to, the openings of channel 15. By not "sealing" D1's apertures to passages 14, passages 14 and 15 may be utilized during the reverse flow or reaction cycle, increasing the overall efficiency of the system. This "open" distributor (D1) can also be utilized in embodiment comprising multiple pyrolysis reactor systems, e.g., those where the reactor/recuperator beds move (e.g., rotate) in and out of a gas stream. FIG. 4A schematically shows an end view of reactor 7, with the shaded regions representing the approximate locations of distributor D1 (utilized to direct fuel into passages 14). The unshaded region corresponds to the approximate locations of passages 15, which are utilized during the oxidation step for conveying oxidant from conduit 3051 to region 13.

During the oxidation step, fuel and oxidant transit the recuperator zone 7, abstracting at least a portion of the heat, stored in the recuperator zone from previous pyrolysis steps. The heated reactants (fuel and oxidant) are then introduced into zone 13 as shown in FIGS. 3 and 4. Mixer-distributor means can be utilized in zone 13 to produce the fourth mixtures by combining the first and second reactants emerging from recuperator zone 7, and then distributes the fourth mixture, particularly the fourth mixture's fuel and oxidant components to achieve a more uniform oxidation over the reactor system's cross section upstream of reaction zone 1. The fourth mixture's oxidant component reacts with (i) the fourth mixture's fuel component and (ii) combustible non-volatiles located in the reactor system to produce a fifth mixture, which can further comprise unreacted fourth mixture, if any.

The total duration of an oxidation step $t_2$ is generally greater than or equal to the time needed for the second reactor to abstract sufficient heat from the oxidation to accomplish the pyrolysis step. In other words, the oxidation step is conducted for a time duration greater than or equal to a time sufficient to displace the peak of the temperature profile toward the second reactor sufficient to heat the pyrolysis region 2064 for exposing the first mixture to a temperature $\geq 1.20 \times 10^{3\circ}$ C. during the pyrolysis step. The value of $t_2$ depends on factors such as the geometry of the reactors utilized in stage 206, the heat transfer characteristics of the reactors and the materials from which the reactors are made, and the amount of heat needed by the pyrolysis step. Optionally, the $t_2$ is in the range of $1.0 \times 1.10^{-3}$ seconds to 10.0 seconds. In an embodiment, $t_2$ is greater than or equal to the time needed to heat the pyrolysis region 2063 to a temperature sufficient for exposing ≥50.0 wt. % of the first mixture, e.g., ≥75.0 wt. %, such as ≥90.0 wt. % to a temperature $\geq 1.20 \times 10^{3\circ}$ C. during the pyrolysis step; the weight percents being based on the weight of the first mixture. In an embodiment, $t_2$ is ≤10.0 seconds, e.g., ≤5.0 seconds, such as ≤1.0 seconds.

It is understood that flow control means (e.g., one or more of valves, rotating reactor beds, check valves, louvers, flow restrictors, timing systems, etc.) can be used to control gas flow, actuation, timing, and to alternate physical beds between the flow systems for the first, second, fourth, and fifth mixtures, and the optional purge gas when used between one or more of the steps. Suitable spargers, distributors, etc. are disclosed in U.S. Pat. No. 7,815,873; which is incorporated by reference herein in its entirety. Although the invention is compatible with the use of conventional spargers, distributors, plenums, etc., in stage 206, the invention is not limited thereto. The fourth and fifth mixture will now be described in more detail.

Fourth Mixture

The fourth mixture comprises first and second reactants. The first reactant can comprise, e.g., ≥10.0 wt. % fuel based on the weight of the first reactant, such as ≥50.0 wt. % fuel. The second reactant can comprise, e.g., ≥10.0 wt. % oxidant based on the weight of the second reactant, such as ≥20.0 wt. % oxidant. The first reactant can be derived from the same source materials utilized for deriving the first mixture. Optionally, the first reactant has substantially the same composition as the first mixture.

Referring again to FIG. 2, Stage 302 can be utilized for adjusting the compositions of source materials 300 to produce the fuel and/or oxidant. Generally, separate fuel and oxidant conduits are utilized (not shown), and optionally the fuel source material is upgraded in a stage (e.g., 302a, not shown) that is different from that used to upgrade the oxidant (302b, not shown). Conduits (represented by line 3021) can be utilized for adding to the fuel source materials one or more of diluent, carbon monoxide, molecular hydrogen, and/or light saturated hydrocarbon. Conduits (also represented by line 3021) can be utilized for adding additional or supplemental oxidant to the oxidant source materials. Undesired species such as heteroatom species can be conducted away from stage 302 by one or more conduits (not shown).

The fuel and oxidant can be the same as those disclosed in U.S. Pat. No. 7,943,808. Optionally, the fuel is derived from, comprises, consists essentially of, or consists of one or more of hydrogen, CO, methane, methane containing streams such as coal bed methane, biogas, associated gas, natural gas, and mixtures or components thereof, etc. Exothermically reacting the first reactant's fuel component and the second reactant's oxidant component provides at least a portion of the heat utilized by the pyrolysis, e.g., ≥50%, such as ≥75%, or ≥95% of the heat utilized by the pyrolysis. Additional heat, when needed, can be provided to the regenerative, reverse-flow pyrolysis reactor by, e.g., a burner or furnace, e.g., a furnace external to the reactor, but in thermal communication therewith. The first and second reactants mix within the regenerative, reverse-flow pyrolysis reactor to produce the fourth mixture, the fuel and oxidant then reacting, e.g., by an oxidation reaction such as combustion, as the fourth mixture traverses at least a portion of the pyrolysis reactor. The first reactant comprises fuel, e.g., molecular hydrogen, synthesis gas (mixtures of CO and $H_2$), or hydrocarbon, such as ≥10.0 wt. % hydrocarbon (including mixtures thereof), or ≥50.0 wt. % hydrocarbon, or ≥90.0 wt. % hydrocarbon based on the weight of the first reactant. The second reactant comprises oxidant, e.g., molecular oxygen.

The amount of oxidant in the second reactant and the relative amounts of first and second reactants utilized to produce the fourth mixture can be specified in terms of the amount of oxidant in the second reactant needed for oxidizing combustible non-volatiles in the reactor system ("X") and the amount needed for the substantially stoichiometric oxidation of the first reactant's fuel component ("Y"). In an embodiment, the total amount of oxidant in the fourth mixture is $Z(X+Y)$, wherein Z is in the range of 0.8 to 10.0, e.g., in the range of 1.0 to 3.0, and the amounts X and Y are on a molar basis. When $Z>1.0$, the excess oxidant can be utilized, e.g., for moderating the reaction temperature during the oxidation step as disclosed in U.S. Pat. No. 7,943,808, and/or for conveying heat within the reactor system.

The fourth mixture is generally produced in the mixing-distribution zone, the mixing-distribution zone being located downstream of the first reactor's channels. Although the fourth mixture comprises the combination of first reactant and second reactants, the combined stream generally includes species resulting from the oxidation of combustible non-volatiles located in the first reactor's passages. Optionally, the combined stream further comprises species resulting from reaction of the first and second reactants in one or more of the first reactor's channels, or locations upstream thereof, as a result of comingling of the first and second reactants. Generally, the amount of comingling is small, as disclosed in U.S. Pat. No. 7,943,808. It can be beneficial for the amount of oxidant in the fourth mixture to exceed that needed to oxidize substantially all of the fourth mixture's fuel component, e.g., for (i) oxidizing combustible non-volatiles located in regions of the reactor system downstream of the first reactor's channels, (ii) moderating the temperature during the oxidation of the fourth mixture's fuel component, and/or (iii) transferring heat within regions of the reactor system downstream of the mixing-distribution zone. The desired amount of excess oxygen can be provided by increasing the relative amount of oxidant in the second reactant and/or by increasing the relative amount of second reactant in the fourth mixture.

Optionally, the fourth mixture further comprises diluent, e.g., ≥1.0 wt. % of diluent based on the weight of the fourth mixture. Suitable diluents (which can be a diluent mixture) include one or more of, e.g., oxygenate (water, carbon dioxide, etc.), non-combustible species such as molecular nitrogen ($N_2$), and fuel impurities such as hydrogen sulfide. In an embodiment, the fourth mixture comprises ≤96.0 wt. % diluent, e.g., in the range of 50.0 wt. % to 95.0 wt. % diluent, based on the weight of the fourth mixture. In an embodiment, diluent is provided to the fourth mixture as a component of the second reactant. For example, the second reactant can comprise 60.0 mole % to 95.0 mole % diluent and 5.0 mole % to 30.0 mole % oxidant per mole of the second reactant, such as when the second reactant is air. Optionally, the second reactant has a mass ratio of diluent to oxidant in the range of 0.5 to 20.0, e.g., in the range of 4.0 to 12.0. It can be beneficial for the second reactant (and fourth mixture) to further comprise diluent, e.g., for (i) moderating the temperature during the oxidation of the fourth mixture's fuel component and/or (ii) transferring heat within the reactor system.

In an embodiment, the first reactant comprises ≥90.0 wt. % molecular hydrogen based on the weight of the first reactant and the second reactant comprises ≥90.0 wt. % air based on the weight of the second reactant. When the second reactor comprises ≥90.0 wt. % air based on the weight of the second reactant, a fourth mixture produced from these can comprise, e.g., ≥1.0 wt. % molecular oxygen, e.g., in the range of 5.0 wt. % to 25.0 wt. %, such as 7.0 wt. % to 15.0 wt. %; ≥0.1 wt. % fuel, e.g., in the range of 0.2 wt. % to 5.0 wt. %, the weight percents being based on the weight of the fourth mixture, with the balance of the fourth mixture being molecular nitrogen diluent, e.g., ≥50.0 wt. % diluent, such as in the range of 60.0 wt. % to 94.50 wt. % diluent based on the weight of the fourth mixture.

In an embodiment, the mass flow rate of the fourth mixture during the oxidation step is ≥1.0 times the flow rate of the first mixture during the pyrolysis step, e.g., in the range of 1.0 to 6.0 times the flow rate of the first mixture during the pyrolysis step.

Fifth Mixture

The fifth mixture comprises (i) products derived from the exothermic reaction of the fourth mixture's fuel and oxidant with each other and with the combustible non-volatiles within the reactor, optionally (ii) diluent, when diluent is present in the fourth mixture, and/or (iii) unreacted fuel and oxidant. When the exothermic reaction of the fuel and oxidant involves hydrocarbon combustion, or when a diluent is present in the fourth mixture (such as $N_2$ or $H_2S$), the fifth mixture can comprise carbon dioxide, and can further comprise sulfur oxides, nitrogen oxides, etc.

As shown in FIG. 2, the process can also include an upgrading stage 308 for upgrading the fifth mixture downstream of conduit 2066. One or more conduits 3081 can be utilized for conducting away combustion products and upgraded combustion products away from stage 308, e.g., one or more of non-oxidized hydrocarbon, oxygenate, or heteroatom species such as $NO_x$, $SO_x$, $N_2$, sulfuric acid, etc.

Stages Downstream of the Pyrolysis Stage

As shown in FIG. 2, the second mixture or a vapor-phase component thereof (e.g., the third mixture) is conducted away from stage 206 via conduit 2065 to stage 208, stage 208 being utilized for separating the sixth and seventh mixtures. In one embodiment, the sixth and seventh mixtures are separated from the second or third mixture by solvent extraction.

For example, acetylene can be extracted from the vapor-phase portion of the second mixture in stage 208 using a polar fluid, the polar fluid being conducted to stage 208 via conduit 2086. At least a portion of the extract's acetylene is then removed from the polar fluid to produce the sixth mixture, with the polar fluid being returned to line 2086 for re-use, as shown. The sixth mixture is conducted away from stage 208 via conduit 2087. The polar fluid can remove, e.g., ≥50.0 wt. %, e.g., ≥90.0 wt. %, such as ≥95.0 wt. % of the second mixture's acetylene, based on the weight of the second mixture's acetylene. The polar fluid can comprise, e.g., one or more of furfural, phenol, n-methyl-2-pyrrolidone, methanol, acetone or tetrahydrofuran. Suitable polar fluids are disclosed in U.S. Pat. Nos. 3,093,697; 3,617,495; 4,274,841; and 7,045,670, which are incorporated by reference herein in their entirety. At least a portion of the raffinate's (i) molecular hydrogen and (ii) carbon monoxide are utilized to produce the seventh mixture. The seventh mixture is conducted away from stage 208 via conduit 2081.

Stage 208 can have, e.g., at least two broad functions. The first function is to remove poisons, impurities (e.g., hydrogen sulfide), or excess species (e.g., molecular hydrogen) that are not needed by downstream conversion, and the second function is to direct by splitting or separation the flows of downstream reactants (e.g., acetylene, carbon monoxide, and/or molecular hydrogen) to designated conversion stages (e.g., 210, 214). The functions may be effected in any order, may be affected by single or multiple process steps. The first function may be applied even when no division of the downstream reactants is made, and/or prior to or after the splitting and separating of downstream reactants. The sixth and seventh mixtures will now be described in more detail. Heteroatom species and olefin (such as ethylene) can be conducted away from stage 208 via one or more conduits 2082.

The sixth mixture, which comprises acetylene, is conducted to stage 214 for conversion of at least a portion of the sixth mixture's acetylene to a first intermediate comprising aromatics, e.g., a first intermediate comprising ≥50.0 wt. % of, e.g., benzene and/or toluene based on the weight of the sixth mixture. Optional stage 216 can be utilized for removing and conducting away via conduit 2162 molecules that are not needed in stages downstream of stage 214, e.g., unconverted acetylene.

Conventional methods can be utilized for converting acetylene to aromatics in stage 214, but the invention is not limited thereto. For example, acetylene can be converted to benzene utilizing methods disclosed in U.S. Patent Application Publication No. 2009/0287031A1, which is incorporated by reference herein in its entirety. These methods can involve diluting the acetylene with, e.g., inert gases or dissolved in solvents to keep it out of the decomposition regime, as disclosed in U.S. Pat. No. 2,912,472. In accordance with these methods acetylene can be mixed with other gases, e.g., methane, hydrogen, and/or carbon dioxide, and then exposed to a temperatures in the range of 600° C. to 1000° C. and a space velocity (LHSV) of 400 $h^{-1}$ to 5000 $h^{-1}$. One or more tube furnaces can be used to do this, for example. Another suitable method for converting acetylene to benzene (the "Reppe Method") is disclosed in Justus Liebigs Annalen der Chemie, vol. 560, pp. 104-116 (1948). The Reppe Method involves combining benzene and a benzene-soluble nickel catalyst, such as bis(triphenylphosphine)dicarbonylnickel. Acetylene is added to the benzene-catalyst mixture, which is then exposed to a temperature in the range of 60° C. to 150° C. at a pressure in the range of from 1 MPa to 3 MPa. Heterogeneous catalytic methods can also be used to convert acetylene into benzene, including conventional methods utilizing heterogeneous catalysis such those disclosed in U.S. Pat. Nos. 4,424,401; 2,846,490; and 3,365,510. For example, acetylene can be combined with isobutene and converted to aromatics utilizing, e.g., (i) cobalt oxide deposited on silica-alumina, a temperature in the range of 10° C. to 100° C., a pressure in the range of 2 MPa to 5 MPa, and a space velocity (LHSV) in the range of 0.1 $h^{-1}$ to 15 $h^{-1}$; or (ii) a zeolite catalyst, at a temperature in the range of 260° C. to 450° C., a pressure in the range of 0.05 to 5 MPa, and a space velocity (WHSV) of 0.1 $h^{-1}$ to 20 $h^{-1}$. The first intermediate can be conducted to stage 218 via conduit 2161.

The seventh mixture generally comprises molecular hydrogen and carbon monoxide, e.g., ≥1.0 wt. % molecular hydrogen and ≥7.0 wt. % carbon monoxide based on the weight of the seventh mixture, such as such as ≥5.0 wt. % molecular hydrogen and ≥35.0 wt. % carbon monoxide, or ≥10.0 wt. % molecular hydrogen and ≥70.0 wt. % carbon monoxide, or about 12.5 wt. % molecular hydrogen and about 87.5 wt. % carbon monoxide. At least a portion of the second mixture's molecular hydrogen and carbon monoxide are converted in stage 210 to a second intermediate comprising alcohol, e.g., ≥50.0 wt. % methanol, or ≥90.0 wt. % methanol, based on the weight of the second intermediate. Stage 210 can include means for removing from the second mixture (or third mixture) molecules that are not utilized in producing alcohol, e.g., excess molecular hydrogen or excess carbon monoxide. Optionally, the molar ratio of molecular hydrogen to carbon monoxide is in the range of 1 to 10 molecular hydrogen molecules per carbon monoxide molecule, e.g., 2 to 8 molecular hydrogen molecules, such as about 2 molecular hydrogen molecules per carbon monoxide molecule. If the seventh mixture does not contain molecular hydrogen and carbon monoxide in the desired relative amounts, the seventh mixture's composition can be adjusted in stage 210, e.g., by adding or removing carbon monoxide or molecular hydrogen. Alternatively, and preferably, the relative amount of oxygenate in the first mixture is adjusted up or down (optionally, with different pyrolysis conditions in stage 206, as described above) in order to bring the seventh mixture's molecular hydrogen:carbon monoxide ratio into the desired range.

Conventional methanol synthesis methods can be utilized in stage 210, but the invention is not limited thereto. For example, stage 210 can utilize one or more catalysts comprising copper oxide and/or zinc oxide (optionally further comprising an alumina-containing support), such as those disclosed in Great Britain Patent No. 1159035. Reaction conditions can include, e.g., a temperature in the range of from of 200° C. to 300° C., a pressure in the range of 5 MPa to 10 MPa, and a space velocity (LHSV) in the range of 5000 $h^{-1}$ to 50,000 $h^{-1}$. Optional stage 212 can include, e.g., means for removing exit gases (e.g., for use as a fuel in stage 206) and/or non-methanol components of the second intermediate. These can be conducted away via one or more conduits 2122, for example. The second intermediate can be conducted away from stage 212 via conduit 2121, for example.

In an embodiment, at least a portion of the first intermediate's aromatics are reacted with a least a portion of the second intermediate's methanol in stage 218 to produce a product comprising xylenes and water. For example, when the sixth mixture comprises ≥90.0 wt. % benzene based on the weight of the sixth mixture and the seventh mixture comprises ≥90.0 wt. % methanol based on the weight of the methanol, reacting the sixth and seventh mixtures at a molar ratio of 1:2 (benzene:methanol) results in a product comprising xylenes and water at a molar ratio of 1:2 (1 mole of xylene per 2 moles of water). Stage 218 can utilize conventional methods for reacting the sixth and seventh mixtures, e.g., those utilizing a zeolite catalyst, but the invention is not limited thereto. For example, in one embodiment, stage 218 utilizes the method disclosed in U.S. Pat. No. 6,504,072, which is incorporated by reference in its entirety.

When the sixth and seventh mixtures are reacted according to the method of U.S. Pat. No. 6,504,072, the first product generally comprises ≥50.0 wt. % p-xylene, based on the weight of the first product's xylenes, e.g., ≥75.0 wt. %, such as ≥90.0 wt. %. According to that method, benzene and methanol are reacted in the presence of a catalyst which comprises a porous crystalline material having a Diffusion Parameter for 2,2-dimethylbutane in the range of about 0.1 $sec^{-1}$ to 15 $sec^{-1}$, when measured at a temperature of 120° C. and a 2,2-dimethylbutane pressure of 60 torr (8 kPa).

The porous crystalline material can be, e.g., a medium-pore size aluminosilicate zeolite, such as those having a pore size of about 5 Å to about 7 Å. Medium-pore size aluminosilicate zeolites and other medium pore acidic metallosilicates, such as silicoaluminophosphates (SAPOs), can be used in the process. Particular examples of suitable medium pore zeolites include ZSM-5, ZSM-11, ZSM-12, ZSM-22, ZSM-23, ZSM-35, ZSM-48, and MCM-22, with ZSM-5 and ZSM-11 being particularly preferred.

The process of reacting the aromatics and methanol may suitably be carried out in fixed, moving, or fluid catalyst beds, and can include, e.g., a temperature in the range of 500° C. and 700° C., a pressure in the range of 0 psig to 1000 psig (about 100 kPa to about 7000 kPa), a weight hourly space velocity in the range of 0.5 and 1000, and a molar ratio of benzene to methanol (in the reactor charge) of at least about 0.2, e.g., from about 0.2 to about 20. The process can be conducted in the presence of added hydrogen and/or added water such that the molar ratio of hydrogen and/or water to benzene methanol in the feed is between about 0.01 and about 10.

Under these conditions, benzene can be alkylated with methanol (twice; one alkylation per pass) so as to produce p-xylene at a selectivity of at least about 90 wt. % (based on total $C_8$ aromatic product) at a per-pass benzene conversion of at least about 15 wt. % based on the weight of feed benzene (first pass) or feed toluene (second pass). Optionally, trimethylbenzene production level is ≤1 wt. % based on the weight of the product.

Optional stage 220 can be utilized for separating, e.g., water from the first product, the water being conducted away from stage 220 via conduit 2202. At least a portion of the first product's xylenes can be conducted away from stage 220 via conduit 2201, for example.

Example

The following prophetic example is conducted. A first mixture is exposed to a time averaged (over the duration of the pyrolysis step) peak pyrolysis temperature of $1.625 \times 10^{3}$° C., for a residence time of about $1.0 \times 10^2$ milliseconds, at a total pressure of 5.0 bar (absolute) to produce a second mixture; the first mixture comprising 68.5 wt. % of methane, 17.1 wt. % of molecular hydrogen, and 14.4 wt. % of carbon monoxide (Effectiveness Factor of 1.0) based on the weight of the first mixture; and the second mixture comprising 18.1 wt. % of acetylene, 11.8 wt. % of ethylene, 20.5 wt. % of methane, 1.4 wt. % of ethane, 25.1 wt. % of molecular hydrogen, 8.6 wt. % of $C_{3+}$, and 14.4 wt. % of carbon monoxide based on the weight of the second mixture. For the purpose of this example, it is presumed that the $C_{3+}$ remains in the pyrolysis reactor as a deposit. Acetylene is separated from the second mixture by contacting the second mixture with n-methyl-2-pyrrolidone. The separated acetylene is recovered, thereby producing a sixth mixture, and the n-methyl-2-pyrrolidone is recycled to the separator. A seventh mixture comprising carbon monoxide and molecular hydrogen is separated from the remainder of the pyrolysis product, the remainder comprising 28.0 wt. % of methane, 19.6 wt. % of carbon monoxide, 34.2 wt. % of molecular hydrogen, 1.9 wt. % of ethane, and 16.2 wt. % of ethylene based on the weight of the remainder. Excess molecular hydrogen is conducted away from the seventh mixture, and the remaining molecular hydrogen and carbon monoxide of the seventh mixture are reacted according to the method of Great Britain Patent No. 1159035 to produce a second intermediate comprising ≥90.0 wt. % methanol based on the weight of the second intermediate.

The sixth mixture's acetylene is trimerized according to the method disclosed in U.S. Patent Application Publication No. 2009/0287031A1 to produce a first intermediate comprising ≥90.0 wt. % benzene based on the weight of the first intermediate. The first intermediate's benzene and the second intermediate's methanol are then reacted (two-passes) according to the method of U.S. Pat. No. 6,504,072 to produce a product comprising water and xylenes, the xylenes being ≥90.0 wt. % p-xylene based on the weight of the xylenes.

The invention claimed is:
1. A hydrocarbon conversion process, comprising:
 (a) providing a first mixture, the first mixture comprising ≥25.0 wt. % of methane, ≥5.0 wt. % molecular hydrogen, and an oxygenate, the oxygenate comprises ≥10.0 wt. % of carbon dioxide and/or carbon monoxide, the weight percents being based on the weight of the first mixture;
 (b) exposing the first mixture to a temperature ≥700° C. in a first region under pyrolysis conditions to produce a second mixture, the second mixture comprising molecular hydrogen, carbon monoxide, and ≥1.0 wt. % of acetylene based on the weight of the second mixture, wherein the second mixture has a molecular hydrogen: carbon monoxide molar ratio ≥2.0 and a carbon monoxide:acetylene molar ratio ≥0.1;

(c) converting at least a portion of the second mixture's acetylene to produce a first intermediate mixture comprising ≥10.0 wt. % aromatic hydrocarbon based on the weight of the intermediate mixture;

(d) reacting at least a portion of the second mixture's carbon monoxide with at least a portion of the second mixture's molecular hydrogen to produce a second intermediate mixture comprising ≥10.0 wt. % alcohol based on the weight of the second intermediate mixture; and (e) reacting at least a portion of the first intermediate mixture's aromatics with at least a portion of the second intermediate mixture's alcohol to produce a product comprising water and ≥10.0 wt, % p-xylene based on the weight of the product.

2. The process of claim 1, wherein the first mixture's hydrocarbon comprises ≥90.0 wt. % methane, based on the weight of the first mixture's hydrocarbon, and the first mixture's oxygenate further comprises ≥90 wt. % of one or more of carbon monoxide, water, molecular oxygen, carbon dioxide, methanol, or ethanol, based on the weight of the first mixture's oxygenate.

3. The process of claim 1, wherein the first mixture's oxygenate comprises ≥5.0 wt. % of carbon dioxide.

4. The process of claim 1, wherein the pyrolysis conditions include thermal pyrolysis conditions.

5. The process of claim 1, wherein the pyrolysis conditions include high-severity pyrolysis conditions.

6. The process of claim 1, wherein the first mixture's hydrocarbon comprises ≥95.0 wt. % methane, based on the weight of the first mixture's hydrocarbon, and wherein the pyrolysis conditions comprise a peak pyrolysis temperature ranging from 1400° C. to 1800° C., a pressure in the range of from 1.3 bar to 2.0 bar (absolute), and a first mixture residence time in the range of from about 1.0 milliseconds to 50.0 milliseconds.

7. The process of claim 1, wherein the second mixture has an acetylene:ethylene molar ratio in the range of 2.0 to 10.0; a molecular hydrogen:acetylene molar in the range of 3.0 to 20.0.

8. The process of claim 1, wherein the second mixture comprises 2.0 wt. % to 50.0 wt. % methane; 5.0 wt. % to 35.0 wt. % carbon monoxide; 2.0 wt. % to 50.0 wt. % molecular hydrogen; 2.0 wt. % to 40.0 wt. % acetylene; and ≥1.0 wt. % $C_{3+}$, the weight percents being based on the weight of the second mixture.

9. The process of claim 2, wherein the first mixture's oxygenate comprises ≤1.0 wt. % of carbon dioxide and wherein the second mixture (i) comprises ≤10.0 wt. % water based on the weight of the second mixture and (ii) has a carbon dioxide:$C_2$ unsaturates molar ratio ≤0.30.

10. The process of claim 1, further comprising separating a third mixture from the second mixture upstream of steps (c) and (d), the third mixture comprising the portion of the second mixture's acetylene converted in step (c) and the portion of the second mixture's carbon monoxide reacted in step (d).

11. The process of claim 10, wherein the third mixture has substantially the same composition as the second mixture's vapor-phase component.

12. The process of claim 10, wherein the third mixture comprises 1.0 mole % to 35 mole % carbon monoxide, 10.0 mole % to 80.0 mole % molecular hydrogen, and 1.0 mole % to 35.0 mole % acetylene, the mole percents being based on the number of moles of carbon monoxide, molecular hydrogen, and acetylene per mole of the third mixture.

13. The process of claim 10, wherein the third mixture comprises 0.1 wt. % to 50.0 wt. % acetylene, 0.0 wt. % to 50.0 wt. % ethylene, 1.0 wt. % to 60.0 wt. % carbon monoxide, and 0.1 wt. % to 30.0 wt. % molecular hydrogen, based on the weight of the third mixture, wherein the amount of molecular hydrogen is in the range from 0.2 to 20.0 times the stoichiometric amount needed for converting ≥90% (molar basis) the third mixture's carbon monoxide to methanol.

14. The process of claim 10, wherein the third mixture has an amount of carbon monoxide and acetylene that is substantially stoichiometric for (i) converting ≥90.0 wt. % of the third mixture's acetylene to benzene in step (c), based on the weight of the third mixture's acetylene; (ii) for converting for ≥90.0 wt. % of the third mixture's carbon monoxide to methanol in step (d), based on the weight of the third mixture's carbon monoxide; and (iii) for converting ≥90.0% of the benzene (weight basis) and ≥90.0% (weight basis) of the methanol to the product's p-xylene.

15. The process of claim 1, wherein the pyrolysis of step (b) is conducted in a first region of a pyrolysis reactor, and further comprising:

(f) providing a fourth mixture, and at least partially oxidizing the fourth mixture in a second region of the pyrolysis reactor to produce a fifth mixture, the first and second regions being at least partially coextensive; wherein:

(i) the fourth mixture comprises fuel and oxidant;

(ii) the fifth mixture comprises water and/or carbon dioxide; and (iii) the exposing of the first mixture and the oxidizing of the fourth mixture occur at substantially different times.

16. The process of claim 15, further comprising repeating steps (a)-(f) in sequence, wherein (i) at least a portion of the fifth mixture is conducted away from the second region before step (a) and (ii) the exposure temperature in the first region results at least in part from the heat generated during the oxidizing of the fourth mixture in the second region.

17. The process of claim 15, further comprising at least one of:

(i) separating from the fifth mixture a byproduct comprising oxygenate and utilizing at least a portion of the separated byproduct to produce the first and/or fourth mixtures; or (ii) separating from the second mixture a second byproduct comprising hydrocarbon and hydrogen and utilizing at least a portion of the separated second byproduct to produce the first and/or fourth mixtures.

18. The process of claim 1, further comprising contacting the second mixture with a diluent having an affinity for acetylene to produce an extract comprising at least a portion of the second mixture's acetylene and a raffinate comprising at least a portion of the second mixture's molecular hydrogen and carbon monoxide, and (i) utilizing at least a portion of the extract's acetylene for the conversion of step (c) and/or (ii) reacting at least a portion of the raffinate's molecular hydrogen with at least a portion of the raffinate's carbon monoxide in step (d).

19. The process of claim 1, wherein the converting of step (c) includes a temperature in the range of 600° C. to 1000° C. at a space velocity (LHSV) of 400 h$^{-1}$ to 5000 h$^{-1}$; and wherein the aromatic hydrocarbon comprises ≥90.0 wt. % benzene based on the weight of the aromatic hydrocarbon.

20. The process of claim 1, wherein the converting step (d) includes a temperature in the range of from of 200° C. to 300° C., a pressure in the range of 5 MPa to 10 MPa, and a space velocity (LHSV) in the range of 5000 h$^{-1}$ to 50,000 h$^{-1}$; and wherein the alcohol comprises ≥90.0 wt. % methanol, based on the weight of the alcohol.

21. The process of claim 1, wherein the pyrolysis of step (b) is conducted in at least one regenerative, reverse-flow, thermal pyrolysis reactor.

22. The process of claim 1, wherein the first intermediate mixture comprises ≥75.0 wt. % benzene based on the weight of the first intermediate mixture; the second intermediate mixture comprises ≥75.0 wt. % methanol based on the weight of the second intermediate mixture; and the product comprises ≥25.0 wt. % p-xylene.

23. The process of claim 1, further comprising utilizing at least a portion of the product's water to produce the first mixture's oxygenate.

* * * * *